United States Patent [19]

Kadowaki et al.

[11] 4,365,087
[45] Dec. 21, 1982

[54] PRODUCTION OF ACRYLIC ACID

[75] Inventors: Koju Kadowaki; Kohei Sarumaru, both of Ibaraki; Takeshi Shibano, Yokkaichi, all of Japan

[73] Assignee: Mitsubishi Petrochemical Company Limited, Japan

[21] Appl. No.: 116,445

[22] Filed: Jan. 29, 1980

[30] Foreign Application Priority Data

Jan. 30, 1979 [JP] Japan .................................. 54-8766

[51] Int. Cl.³ ...................... C07C 51/25; C07C 57/04; C07C 57/055
[52] U.S. Cl. ................................. 562/534; 562/532; 562/535; 562/536; 562/544; 562/546; 562/548; 562/600; 568/479
[58] Field of Search .............. 562/532, 535, 534, 546; 260/604 R, 413; 568/479

[56] References Cited

U.S. PATENT DOCUMENTS

| | | | |
|---|---|---|---|
| 3,903,149 | 9/1975 | Kadowaki et al. | 562/534 |
| 4,008,280 | 2/1977 | Watanabe et al. | 568/479 |
| 4,031,135 | 6/1977 | Engelbach et al. | 562/534 |
| 4,147,885 | 4/1979 | Shimizu et al. | 562/535 |

FOREIGN PATENT DOCUMENTS 939713 10/1963 United Kingdom ............... 562/545

*Primary Examiner*—Vivian Garner
*Attorney, Agent, or Firm*—Robert E. Burns; Emmanuel J. Lobato; Bruce L. Adams

[57] ABSTRACT

In the production of acrylic acid by a two-stage, vapor-phase catalytic oxidation of propylene, a composite oxide catalyst expressed by the formula $Mo_aBi_bNi_cCo_dFe_eNa_fMn_gB_hK_iSi_jO_x$ is used in the first-stage reaction, which is carried out under specific reaction and operational conditions, and the second-stage reaction is carried under specific reaction and operational conditions while oxygen is supplied by a specific mode.

7 Claims, No Drawings

PRODUCTION OF ACRYLIC ACID

BACKGROUND OF THE INVENTION

This invention relates generally to the production of acrylic acid by vapor-phase catalytic oxidation of propylene in two stages. More particularly, the invention relates to an industrially safe and economical process for producing acrylic acid by the above mentioned oxidation in which a number of hitherto unsolved problems, as described hereinafter, are overcome by the use of a specific catalyst and the selection of specific reaction conditions or operational conditions in the first-stage reaction and by the supply of oxygen by a specific mode and the selection of specific reaction or operational conditions in the second-stage reaction.

As a process for producing acrylic acid, the method of vapor-phase catalytic oxidation of propylene in two stages with the use of air is known and is already being industrially practiced. In the first stage of this process, propylene is mixed with air and steam or an inactive gas such as nitrogen and then the mixed gas is supplied thereby to convert the propylene principally into acrolein and a by-product quantity of acrylic acid, and the outlet gas of this first stage is supplied, without separation of the formed products, to the reaction vessel of the second stage, in which the acrolein is principally converted into acrylic acid. The acrylic acid thus formed is, in general, cooled and recovered as an aqueous solution from the gas stream and, in the succeeding purification step, is subjected to an extraction, distillation, or like process step and is thereby isolated. As an alternative procedure, a method wherein the gas stream from the outlet of the second stage is cooled, and then acrylic acid is absorbed with a suitable solvent and thereby separated has been proposed.

In this series of process steps, the performance of the oxidation catalyst thereof greatly influences the production economy, and, accordingly, numerous proposals with respect to the catalysts of each stage have been made. It may be considered that the performances of these catalysts in terms of the yield of the objective acrolein or acrylic acid are generally amply high on the economical view point. The production of the objective products with high yields of 90 percent or higher are reported, for example, in Japanese Patent Publication Nos. 17711/1972, 27490/1972, 41329/1972, 42241/1972, 42813/1972, 1645/1973, 4763/1973, 4764/1973, and 4765/1973 with regard to first-stage catalysts and, with regard to second-stage catalysts in Japanese Patent Publication Nos. 12129/1969, 19296/1973, 169/1974, 11371/1974, 10432/1977, and 31326/1977 and in Japanese Patent Laid Open Nos. 2011/1971, 8360/1972, 43922/1974, 61117/1974, 124016/1974, 133317/1974, 25520/1975, 93918/1975, 23589/1977, 29483/1977, and 29484/1977. However, in the case of industrial production of acrylic acid with the use of these catalysts, various difficulties are encountered with the realization of necessary industrial conditions other than the yield of the objective product.

One of these problems is that, although there is the necessity of obtaining the objective product with an amply high productivity, that is, space time yield, if the propylene concentration in the starting material is made high for this purpose, there will be a restriction due to the explosion limit, and a quantity of oxygen sufficient for obtaining the objective product cannot be supplied. Consequently, the conversion of the propylene or acrolein will drop, and the single-pass yield will decrease, or hot spots are readily produced at inlet part of the catalyst bed, whereby there is the danger of a runaway temperature rise, and, in addition, a deterioration of the catalyst is caused by the excessive generation of heat.

In this connection, as a measure for preventing the production of hot spots, the measure, simply stated, of diluting the catalyst at parts of great generation of heat with another inactive material, as described in Japanese Patent Publication No. 9859/1959, for example, has been known as a general method. A measure for this purpose with the object of producing acrylic acid is disclosed in, for example, Japanese Patent Laid Open No. 127013/1976.

On the other hand, propylene and acrolein upon being mixed with air produce explosive gases. For this reason, in order to avoid the forming of these explosive gases and, at the same time, to introduce oxygen in the quantity necessary for the reaction, it has been the general practice to add an inactive gas such as nitrogen or steam, particularly steam. However, when the quantity of steam is great, the concentration of the aqueous solution of acrylic acid obtained decreases, and, as a consequence, disadvantages such as an increase in the cost of separating the acrylic acid or an increase in the recovery loss arise.

As a solution for these problems, the method of recycling the residue gas remaining after the acrylic acid and water have been recovered and separated by cooling, absorption or scrubbing with a solvent or like measure from the gases formed in the reaction (the residue gas comprising, principally, nitrogen, carbon dioxide, carbon monoxide, etc., and, in addition, unreacted propylene, acrolein, oxygen, etc.), substituting this residue gas for steam thereby increasing the acrylic acid concentration of the aqueous solution thus obtained naturally appears to be suitable and has been disclosed in, for example, Japanese Patent Publication No. 30688/1978 and Japanese Patent Laid Open Nos. 36415/1976, 108917/1977, 15314/1978. However, since the composition of the exhaust gases depends on the reaction conditions and thus fluctuates, this method is accompanied by the problem of complicated operational control and procedure for avoiding the explosive range due to this gas recycling and of the danger.

As a measure for increasing the space time yield, the method of carrying out the reaction by increasing the space velocity thereby to shorten the contact time appears at first sight to be suitable. However, since the reaction temperature in this case is high as a natural result, the selectivity of the reaction tends to decrease, and, in addition, the catalyst life is shortened. Furthermore, operation on the high-temperature side is disadvantage also because of combustion reaction of runaway character in the empty parts of the reaction vessel due to spontaneous or autogenous oxidation of the acrolein described hereinafter.

Another method of increasing the space time yield is to use a high reaction pressure thereby to increase the process quantity per unit time. This method is effective up to a certain pressure range. However, when the pressure becomes high, the molecular diffusion velocity decreases. For this reason, the diffusion resistance between the bulk of the gas stream and the catalyst surface increases, and, as a result, the yield of the objective product is lowered, whereby the use of this method is limited.

A second difficult problem accompanying the production on an industrial scale of acrylic acid by catalytic oxidation of propylene in two stages is how to avoid or lessen the danger of occurrence of a runaway combustion reaction, which may be considered to arise from spontaneous oxidation of acrolein, at the outlet vapor-phase part of the first-stage reaction. As a result of our experiments, we have found that this combustion occurs when acrolein coexists with oxygen and that the higher the gas temperature, the higher the partial pressure of the acrolein, and the longer the retention time because of large space volume, the higher will the reaction rate become and give rise to a rapid and violent combustion.

Accordingly, in order to attain a high space time yield and carry out production under safe conditions, a correspondingly proportionate countermeasure technique is required. As measures intended to solve these problems, the following methods, for example, are known. Japanese Patent Laid Open No. 36415/1976 discloses a method which comprises cooling the outlet gas stream of the second stage in the method of oxidizing propylene in two stages, recovering the acrylic acid formed in an aqueous solution thereof, thereby separating and recovering the same, and recycling the residual gas stream by dividing it into portions respectively for the first and second stages. As a countermeasure for the acrolein combustion at the first-stage outlet in this method, it is proposed to "add and mix air and waste gas to and with the reaction gas mixture immediately after it has come out of the catalyst zone of the first stage with rapid cooling to a temperature of the mixture of 150° to 320° C.".

This disclosure suggests an effective method as one countermeasure for the acrolein combustion, but, as far as we are aware, since it is necessary to supply to the first and second stages the waste gas and air in quantities controlled to be within specific ranges, a very complicated control procedure is required when carrying out an unsteady-state operation such as that during start-up or shut-down of the plant while avoiding the explosive range, and the operation entails danger. Particularly since the quantity of residual oxygen in the waste gas differs with the reaction rate of each stage as mentioned hereinbefore, it is necessary to constantly monitor the outlet oxygen concentration and responsively control the air supply rate, the recycled gas flow rate, the reaction temperature, and other variables, whereby the operational procedure would be complicated.

Furthermore, the specified temperature range of 150° to 320° C. can include the range wherein combustion suppression is impossible and may thus be interpreted to be inadequate with respect to the object. While the method described in Japanese Patent Laid Open No. 15314/1978 may also be effective, it is not different, as far as we are aware, from the method described in Japanese Patent Laid Open No. 36415/1976 on the point that the formation of the explosive range in the first-stage reaction is avoided by recycling waste gas.

Thus, while the various proposals described above respectively indicate improvements with respect to problems, it is our belief that none of them can yet be said to be satisfactory from the industrial viewpoint.

SUMMARY OF THE INVENTION

It is an object of this invention to provide solutions to the above described problems encountered in the two-stage, vapor-phase catalytic oxidation method. It is contemplated in the practice of this invention to achieve this object by the use of a specific catalyst and the selection of specific reaction conditions or operational conditions in the first-stage reaction and by the supply of oxygen by a specific mode and the selection of specific reaction conditions or operational conditions in the second-stage reaction.

According to this invention there is provided a process for producing acrylic acid by a two-stage, vapor-phase catalytic oxidation which comprises subjecting a mixture gas of propylene, steam, and air to a first-stage reaction thereby to convert the propylene into, principally, acrolein and subjecting the gaseous product formed in the first-stage reaction to a second-stage reaction thereby to convert the acrolein into, principally, acrylic acid, the process being characterized in that said oxidation is carried out under the conditions:

A. that a composite oxide catalyst expressed by the formula

$Mo_aBi_bNi_cCo_dFe_eNa_fMn_gB_hK_iSi_jO_x$, where a through x represent atomic ratios of the respective elements, and when a is 12, b is 4 through 7, c is 0.05 through 5, d is 0.05 through 5, e is 0.05 through 2, f is 0 through 1, g is 0 through 1, (f+g) is 0.01 through 1, h is 0.02 through 2, i is 0 through 1, j is 6 through 48, and x is a number satisfying the valence of an element other than oxygen, is used in the first-stage reaction;

B. that (1) the composition of said mixture gas supplied to a catalyst bed in the first-stage reaction is characterized by an oxygen-propylene mol ratio of (1.1 to 2.0)/1, a propylene concentration of 7 to 13 percent, and a steam concentration of 2 to 30 percent, the temperature of the mixture gas prior to its introduction into the catalyst bed being 260° C. or lower, and (2) the reaction conditions on the first-stage catalyst are a reaction temperature of 260° to 370° C. and a contact time of 1 to 8 seconds, and C. that a second mixture gas of the gaseous product formed in the first-stage reaction and a gas resulting from addition of air or oxygen gas to a waste gas separated from gaseous product formed in the second-stage reaction is supplied to a catalyst bed in the second-stage reaction, (1) the oxygen content of the second mixture gas being such that the mol ratio X/Y, wherein X is the sum of the quantity of oxygen in the mixture gas subjected to the first-stage reaction and the quantity of oxygen thus added to the waste gas, and Y is the quantity of propylene in the mixture gas subjected to the first-stage reaction, will be (1.6 to 2.8)/1, and (2) the temperature of the second mixture gas prior to its introduction into the second-stage catalyst bed being 280° C. or lower, said waste gas being a portion of a waste gas which results from cooling of the gaseous product formed in the second-stage reaction and removal therefrom of a greater part of the acrylic acid therein by condensation.

This invention is based on certain fundamental facts relating to an oxidation process step aimed at establishing an industrially safe and economical method with respect to a process for producing acrylic acid by catalytic oxidation of propylene. That is, this invention is based on a number of new facts which have been discovered as a result of our work including clarification of the characteristics of an improved oxidation catalyst, precise determination of explosive limits, and measurement of the velocity of spontaneous oxidation of acrolein, whereby this invention provides an industrially advantageous process in which the reactant materials and utilities are highly effective, and, at the same time, the operation conditions and control procedures are safe.

DETAILED DESCRIPTION OF THE INVENTION

As mentioned above, this invention relates to the production of acrylic acid by vapor-phase catalytic oxidation in two stages of propylene. In the process of this invention, the composition of the catalyst used in the first-stage reaction and the reaction conditions or the operational conditions of each stage are specified, but with respect to particulars other than these requisites peculiar to this invention, the conditions disclosed or publicly used in the prior art as described hereinbefore and other references may be utilized within limits which are not contrary to the purport and spirit of this invention.

1. First-stage reaction

This invention has a unique characteristic in the catalyst and reaction conditions used in the first stage. In the reaction of the first stage, in order to obtain a high productivity, that is, space time yield of the objective product, the composition of the starting gas mixture is selected to have a high propylene concentration, the minimum quantity of oxygen required for the reaction, and the minimum quantity of a diluent gas required for avoiding the explosive range, and this starting gas mixture is converted with one pass into the objective product in a high yield over a catalyst composition of stable and long life. Specifically: the steam concentration in the mixture gas comprising propylene, steam, and air is 2 to 30 percent, preferably 5 to 25 percent; the oxygen/propylene mol ratio is 1.1 to 2.0/1, preferably 1.2 to 1.8/1; and the propylene concentration is 7 to 13 percent, preferably 8 to 12 percent.

For the diluent gas used for causing the composition to be outside of the explosive range, nitrogen, carbon dioxide, steam, and others are generally used, but according to this invention, the minimum necessary quantity of steam is used because it affords safe operational procedures, maximum effectiveness on the points of explosive limits and thermal conductivity, and, moreover, stable maintenance of the reactivity of the catalyst.

However, this starting gas is accompanied by the danger of decomposition and combustion of propylene when the gas stays in the empty space of the reaction vessel at a high temperature of approximately 300° C. or higher, although the temperature depends on the composition of the gas (reference is made to a Reference Example set forth hereinafter). Therefore, it is necessary to introduce this gas into the reaction vessel at a temperature (of the gas) (after being preheated) of a temperature not higher than 260° C., preferably from 130° to 250° C. For this reason, when it is further necessary to preheat the starting gas up to the reaction temperature required by the catalyst, it is recommended to provide a preheating zone filled with particles of an inactive material such as α-alumina, Alundum, or Carborundum at the inlet part of the reaction tube.

For obtaining acrolein and acrylic acid with a high conversion by using a starting gas of this character, the selectivity of the catalyst must be high. The reason for this is that, unless the selectivity of the catalyst is high, oxygen deficiency will arise, and the conversion cannot be raised by a method such as increasing the reaction temperature. Furthermore, oxygen deficiency may result in a reduction of the catalyst thereby to shorten the life thereof in some cases.

In order to maintain a high performance over a long period under the conditions of a high propylene concentration of 7 to 13 percent and a relatively small quantity of oxygen of an oxygen/propylene mol ratio of 1.1 to 2.0/1, a specially designed catalyst is required. The catalyst composition specified in this invention fulfills these requirements, and it can be said that the process of this invention has become industrially possible for the first time through the use of this specified catalyst composition.

The catalyst used in the first-stage reaction of this invention is expressed by the formula set forth hereinbefore. Provided that the composition of this catalyst is as described hereinbefore, the method of its preparation is not especially limited. One example of preparation of the catalyst is disclosed in an Example set forth hereinafter. Also, by referring to the contents of the various examples of the known art as enumerated hereinbefore, those skilled in the art can easily learn suitable methods of preparation. Furthermore, the use of, in addition to the elements tabulated hereinbefore, carrier materials or diluents such as alumina and Carborundum, which are commonly used in catalysts of this kind, is not to be excluded.

Still another possibility is the use, particularly in the case where a fixed-bed catalyst is used, of a plurality of kinds of catalysts of different compositions for imparting a distribution of catalytic activity in the direction of flow of the reaction gas for a purpose such as suppression of local generation of heat (in which case, these catalysts of a plurality of kinds need not all be of compositions as described hereinbefore). The shape or form of the catalyst may be any of those possible for a catalyst of this kind, but first the pore volume is preferably as large as possible within a range wherein the mechanical strength of catalyst can be maintained for reducing the diffusion resistance within the particles. Furthermore, a shape in which the ratio of exterior area/volume is large such as, for example, a cylinder of small diameter and long axial dimension, a plate-shaped cylinder or tablet, a saddle shape, or a ring shape is suitable.

The reaction of the first stage is carried out with a contact time of 1 to 8 seconds, and a setting of the temperature which results in a propylene conversion of 90 percent or higher is desirable. Shorter contact time than this level will bring on the difficulty in eliminating the reaction heat, and since the temperature is high as a natural result of the reaction rate being made to be 90 percent or higher, the prevention of the spontaneous oxidation of the acrolein at the outlet of the reaction vessel is thus difficult even with the application of the measure of this invention. With a reaction temperature not higher than 370° C., preferably not higher than 350° C., the application of this invention is found to be effective. However, when this temperature falls below 260° C., the propylene conversion drops, and objects are not achieved. The preferred reaction temperature is in the range of 270° to 350° C. When the contact time exceeds 8 seconds, the process is not economical on the point of space time yield. A contact time of 2 to 6 seconds is preferred.

The conversion of the propylene should be at a level such that the total yield of the objective products of the first stage, viz. acrolein and acrylic acid, will be a maximum, and the conversion of 95 percent or higher is ordinarily attained with the use of the instant catalyst. An operation with a propylene conversion of 90 percent or less is not desirable since the concentration of the propylene introduced into the second stage increases to give rise to an increase in the quantity of propionic acid as a by-product and to problems of product quality in some cases.

2. Second-stage reaction

At the outlet of the catalyst bed of the first stage, a gas mixture of a portion of the waste gas which results from the recovery/removal of acrylic acid (and condensable components thereof, for example, water) etc., by cooling the outlet gas stream of the second stage and air or oxygen gas is added to the effluent gas whereby the fluid temperature is cooled to a temperature of 280° C. or lower, preferably 200° to 270° C., while, at the same time, the acrolein partial pressure is lowered. As a result, it becomes possible to suppress to a substantially negligible degree combustion due to the spontaneous oxidation of the acrolein. The cooling to the above mentioned temperature can be accomplished also in conjunction with a method using a heat exchanger.

As a result of our experiments, we have ascertained that the rate of this spontaneous oxidation has a dependency, while there are some differences because of factors such as the shape of the space, in the range of from first to second-order with respect to the acrolein partial pressure, and that the apparent activation energy is remarkably great, being with a range of 35 to 60 Kcal/mol. We have found further that, since the rate of oxidation reaction of the first stage is substantially proportional to the propylene partial pressure, and the activation energy is 8 to 15 Kcal/mol, lowering the reaction temperature with raising the propylene partial pressure is effective to obtain a large space time yield in suppressing spontaneous oxidation.

The quantity of the oxygen added at the outlet of the first stage is the quantity required for the reaction of the second stage, and air or oxygen gas is so supplied that the sum of this quantity and the quantity supplied at the inlet of the first stage will become 1.6 to 2.8 times, preferably 1.7 to 2.6 times, the quantity of propylene supplied at the inlet of the first stage. Since the air or oxygen gas thus added is added as a mixture with waste gas, the mixing with the outlet gas of the first stage also does not form an explosive composition and can be carried out safely.

The mixing of, for example, air as it is with the outlet gas of the first stage is not desirable from the standpoint of safety since there is a possibility of the formation of a local composition within the explosive range of acrolein in the mixing step. The waste gas to be recycled comprises principally nitrogen, carbon dioxide, carbon monoxide, uncondensed water, acetoaldehyde, etc., but depending on the operation conditions, a considerable quantity of unreacted propylene and acrolein are contained in this waste gas. Since this unreacted acrolein is converted into acrylic acid in the second stage, it is possible to obtain a higher acrylic acid yield than in a process wherein there is no recycling. For this reason, it is advantageous to recover the acrolein contained in the condensed aqueous solution of acrylic acid by a suitable method such as stripping by reducing the pressure or blowing air, nitrogen gas, or the like into the solution as a carrier gas and to recycle it by mixing it with the above mentioned waste gas. We have found that a recycled gas quantity within the range of 20 to 70 percent of the gas quantity at the second-stage outlet is effective and, moreover, practical.

There are no special limitations relating to the catalyst used in the second stage, any catalyst being usable provided that, by its use, the conversion of the acrolein becomes 90 percent or higher with a temperature of the order of 220° to 340° C. and a contact time of the order of 0.5 to 6 seconds and that it is a stable catalyst of high acrylic acid selectivity. Examples are molybdenum- and(or) vanadium-based catalysts, particularly multiple-component catalysts. Specific examples are composite oxides comprising molybdenum, vanadium, antimony, nickel, niobium, copper, and the like.

The recovery of acrylic acid from the outlet gas of the second-stage reaction vessel is ordinarily carried out by condensing by cooling the acrylic acid together with water and other condensable materials. This cooling can be carried out by means of a suitable cooler or a cooling device comprising a single stage of a heat exchanger or multiple stages thereof. For preventing polymerization of the acrylic acid during this cooling, there is also a method which comprises adding a polymerization inhibitor to the condensed product liquor and causing this liquor and a product gas previously cooled to the vicinity of its dew point to undergo counterflow contacting thereby to admix the polymerization inhibitor simultaneously with cooling and thereby to separate the condensable materials. The cooling is ordinarily carried out to an extent such that the gas temperature becomes 50° to 5° C. At this temperature, condensable substances other than acrylic acid such as, for example, water and acetic acid produced as a by-product, also condense, and unreacted acrolein also partially dissolves and is contained in the condensate.

It is advantageous, after the condensable materials have been separated, to cause the gas to contact chilled water thereby to absorb yet uncondensed acrylic acid to recover the same. However, if a large quantity of water is used for this purpose, the separation of water in the succeeding process step will be uneconomical, and therefore it is desirable that the quantity of this water be kept at a necessary minimum.

3. Reaction vessels of the two stages and other particulars

There is no special necessity of using high reaction pressures in the first and second stages. Reactions at pressures of 0 to 3 kg./cm.$^2$ gage, preferably 0 to 2 kg.cm.$^2$ gage are suitable for producing the objective product in a high yield.

A reaction vessel of a type of a multitubular or tube-and-shell type heat exchanger is normally used, which comprises a bundle of reactor tubes housed in a shell through which a heating medium is circulated. In the practice of this invention, the use of those having reaction tubes of inner diameters of 15 to 40 mm., preferably 15 to 30 mm. and an arrangement wherein the heating medium and the reaction gas flow concurrently is effective in suppressing local generation of heat and smoothing the reaction temperature. Furthermore, for increasing the space time yield, it is effective to pack the catalyst beforehand in a manner such that its activity per unit volume decreases from the inlet, where the heat generation becomes great, through the middle part of the vessel. For this purpose, an effective method other than that wherein a plurality of catalysts of different activities are used is to simply charge the catalyst while diluting it appropriately with particles of inactive materials such as α-alumina, Alundum, mullite, and Carborundum.

4. Examples of experiments

Certain terms used in this disclosure are defined as follows.

$$\text{Contact time (sec.)} = \frac{\text{Apparent volume (liter) of packed catalyst}}{\text{Volumetric flow rate (liter/hr) of starting gas under reaction temp. and press.}} \times 3{,}600$$

$$\text{Propylene conversion (\%)} = \frac{\text{Mols of supplied propylene} - \text{mols of unreacted propylene}}{\text{Mols of supplied propylene}} \times 100$$

$$\text{Yield of compound } i = \frac{\text{Mols of compound } i \text{ formed} \times \text{No. of carbon atoms of } i \text{ molecule}}{\text{Mols of supplied propylene} \times 3} \times 100$$

$$\text{Selectivity (\%) of compound } i = \frac{\text{Yield of compound } i}{\text{Propylene conversion}} \times 100$$

LIMIT OF HEATING TEMPERATURE OF STARTING GAS

Reference Examples 1 through 4

To the upper and lower ends of a vessel of cylindrical shape made of stainless steel and having an inner diameter of 150 mm. and a length of 350 mm., nozzles for inflow and outflow of gas were installed. A thermocouple for temperature measurement was installed at the center of the middle part of the vessel, and the entire vessel was adapted to be heatable by means of an electric heater. As a starting-material gas a gas mixture comprising 10 percent of propylene, 73 percent of air, and 17 percent of steam was passed through this vessel under a pressure of 1.5 kg./cm.² gage and with a retention time of 4 seconds. The results of reaction of the propylene in the case where the vessel was empty and in the case where particles of an inactive material were used are shown in Table 1.

TABLE 1

| | Reference Example 1 | Reference Example 2 | Reference Example 3 | Reference Example 4 |
|---|---|---|---|---|
| Packed material | none | none | α-alumina balls (5 mm. diam.) | mullite balls (5 mm. diam.) |
| Vessel temp. (°C.) | 350 | 260 | 350 | 350 |
| Propylene conversion (%) | 5.5 | trace | trace | trace |
| $CO_2$ formation | formed | trace | trace | trace |
| Temp. of gas in vessel | gradual rise | no change | no change | no change |

PREPARATION OF FIRST-STAGE CATALYST AND PROPYLENE HIGH-CONCENTRATION REACTION

EXAMPLE 1

941 grams (g.) of ammonium paramolybdate was added to 4 liters of pure water and dissolved by heating. Separately, 71.8 g. of ferric nitrate, 258 g. of cobalt nitrate, and 387 g. of nickel nitrate were added to 600 ml. of pure water and dissolved by heating. With ample agitation, these two solutions were gradually mixed. To this liquid mixture, a solution formed by dissolving by heating 8.5 g. of borax, 3.8 g. of sodium nitrate, and 3.6 g. of potassium nitrate in 400 ml. of pure water was added, and the resulting mixture was amply agitated. To this liquid mixture, a solution formed by dissolving 1,077 g. of bismuth nitrate in an aqueous solution of nitric acid of 120 ml. of nitric acid in 980 ml. of pure water was added, and the resulting liquid was agitated. To this liquid, 640 g. of silica was further added, and the mixture thus obtained was agitated and mixed.

The slurry thus obtained was heated and concentrated into dryness. The resulting solid was decomposed by heating in air atmosphere at 300° C., pulverized, and pelletized into pellets each of 5-mm. diameter and 3-mm. height. These pellets were calcined in air atmosphere at 500° C. for 4 hours and thus made into a catalyst. The composition of this catalyst as calculated from the quantities of the introduced starting materials is an oxide complex having the following atomic ratios with respect to metal components.

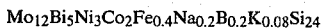

$Mo_{12}Bi_5Ni_3Co_2Fe_{0.4}Na_{0.2}B_{0.2}K_{0.08}Si_{24}$ 250 ml. of this catalyst was mixed with a diluent (mullite balls of 4-mm. dia.) in a ratio of 1:1, and the mixture thus obtained was charged into a reaction tube of an inner diameter of 20 mm. and a length of 2,200 mm. provided with a jacket for a heating medium. Molten salt was used for the heating medium to heat to 310° C. thereby to carry out oxidation reaction of propylene.

The reaction gas, which comprised 10 percent of propylene, 73 percent of air, and 17 percent of steam, was caused to flow over the above described catalyst bed under a pressure at the reaction tube inlet of 1.0 kg./cm.² gage for a contact time of 4.2 seconds. The results are set forth in Table 2.

TABLE 2

| | Propylene conversion (%) | AL yield (%) | AA yield (%) | (AL + AA) selectivity (%) |
|---|---|---|---|---|
| 1st day | 97.8 | 77.3 | 14.1 | 93.5 |
| 30th day | 97.6 | 79.9 | 12.7 | 94.9 |

Abbreviations
AL: acrolein;
AA: acrylic acid

EXAMPLES 2, 3, AND 4

Catalysts of the compositions shown in Table 3 were prepared similarly as in Example 1. The starting material for Mn was manganese borate. Reactions were carried out under the reaction condition of Example 1 except for the bath temperature, whereupon the results shown in Table 4 were obtained.

TABLE 3

| | Catalyst composition (atomic ratio) |
|---|---|
| Example 2 | $Mo_{12}Bi_5Ni_3Co_2Fe_{0.4}B_{0.4}Mn_{0.1}K_{0.08}Si_{24}$ |
| Example 3 | $Mo_{12}Bi_5Ni_3Co_2Fe_1B_{0.4}Mn_{0.1}K_{0.03}Si_{18}$ |
| Example 4 | $Mo_{12}Bi_{6.5}Ni_2Co_2Fe_{0.8}Na_{0.1}B_{0.2}K_{0.08}Si_{18}$ |

TABLE 4

| | Reaction temp. (°C.) | Propylene conversion (%) | AL yield (%) | AA yield (%) | (AL + AA) selectivity (%) |
|---|---|---|---|---|---|
| Example 2 | 305 | 97.5 | 78.5 | 13.5 | 94.4 |
| Example | 300 | 98.2 | 75.8 | 14.6 | 92.1 |

TABLE 4-continued

| | Reaction temp. (°C.) | Propylene conversion (%) | AL yield (%) | AA yield (%) | (AL + AA) selectivity (%) |
|---|---|---|---|---|---|
| 3 | | | | | |
| Example 4 | 310 | 98.3 | 77.9 | 14.2 | 93.7 |

PROPYLENE CONCENTRATION VARIATION IN THE FIRST-STAGE REACTION

EXAMPLES 5 AND 6 AND COMPARISON EXAMPLE 1

With the use of the catalyst of Example 4 and by changing the composition of starting gas for reaction, the variation wih elapse of time of the catalyst performance in the reaction of each composition was tested.

The reaction conditions are shown in Table 5, and the reaction results are shown in Table 6.

| | |
|---|---|
| Reaction tube: | 20-mm. inner diameter, 2,200-mm. length, with heating medium jacket. |
| Quantity of catalyst packed: | 250 ml. (diluted with equal quantity of mullite balls (4-mm. diam.)) |
| Reaction pressure: | 1.0 kg./cm.² gage |
| Contact time: | 4.2 seconds. |

TABLE 5

| | Starting gas composition (%) | | | Bath temp. (°C.) |
|---|---|---|---|---|
| | Propylene | Steam | Air | |
| Example 5 | 8 | 25 | 67 | 310 |
| Example 6 | 12 | 10 | 78 | 310 |
| Comparison Example 1 | 14 | 0 | 86 | 335 |

TABLE 6

| | No. of elapsed days | Propylene conversion (%) | AL yield (%) | AA yield (%) | (AL + AA) selectivity (%) |
|---|---|---|---|---|---|
| Example 5 | 1 | 98.6 | 77.9 | 13.8 | 93.0 |
| | 30 | 97.9 | 81.5 | 11.6 | 95.1 |
| Example 6 | 1 | 97.0 | 74.4 | 14.6 | 91.8 |
| | 30 | 97.1 | 79.3 | 12.8 | 94.9 |
| Comparison Example 1 | 1 | 92.1 | 64.7 | 16.3 | 88.0 |
| | — | — | — | — | — |

By the procedures of Examples 5 and 6, high yields were obtained, and variations of performance with the elapse of time were not observable. On the other hand, it is apparent that by the process of Comparison Example 1, the initial performance was already inferior.

SUPPRESSION OF SPONTANEOUS OXIDATION OF ACROLEIN

EXAMPLE 7, COMPARISON EXAMPLES 2, 3, AND 4

The quantity of spontaneous oxidation of the acrolein at the outlet of the first-stage reaction vessel was measured as follows at different temperatures.

To the stream of gases formed in the first-stage oxidation, in place of the air and recycled waste gas of quantities specified according to this invention, nitrogen gas, which is the predominant component of the waste gas, was mixed and added, and the outlet gas stream of the first-stage reaction vessel was made up. The gas was conducted to a stainless-steel vessel of known interior volume heated by a heating medium, and the quantity of spontaneous oxidation was determined from analysis of the compositions of the inflow gases and the outflow gases.

| Composition of inflow gases | |
|---|---|
| acrolein | 4.68% |
| acrylic acid | 0.75% |
| propylene | 0.12% |
| oxygen | 4.98% |
| steam | 20.07% |
| nitrogen, others | 69.40% |

The interior pressure of the reaction vessel was 2.0 kg./cm.² gage. The conditions and results of the reaction are shown in Table 7.

TABLE 7

| | Vessel capacity (ml.) | Retention time (sec.) | Temp. (°C.) | Spontaneous* oxidation (%) |
|---|---|---|---|---|
| Example 1 | 1100 | 6.5 | 280 | trace |
| Comparison Example 2 | " | " | 300 | 1.0 |
| Comparison Example 3 | " | " | 320 | 4.4 |
| Comparison Example 4 | 300 | 1.8 | 320 | 1.2 |

*Reduction in acrolein yield, based on propylene.

REACTION OF WASTE GAS RECYCLING

EXAMPLE 8

Two multitubular (tube-and-shell) type reaction vessels, each having four stainless-steel reaction tubes each of 20-mm. inner diameter and 3-meter (m.) length and adapted to be heated on its shell side by circulating through the shell a molten nitrate as a heating medium, were directly connected. A nozzle for supplying a mixture gas of waste gas and air was installed immediately after the outlets of the reaction tubes of the first-stage reaction vessel.

The gas from the outlet of the second stage was cooled in a heat exchanger and separated principally into an aqueous solution of acrylic acid and waste gas by means of a gas-liquid separator. After the waste gas was passed through a pressure regulating valve, a portion thereof was passed through an oilless compressor, mixed with air for replenishment, and recycled to the above mentioned nozzle.

A mass of porcelain Raschig rings of 20-cm. layer height was placed in the lower part of the first-stage reaction vessel (reaction gas inlet side). On this mass of Raschig rings, a catalyst of the composition given below prepared by the procedure of Example 4 was placed in a quantity of 700 ml. per reaction tube, 200 ml. on the inlet side being diluted with 100 ml. of Raschig rings, and the space at the upper part of the reaction tube was filled with a mass of Raschig rings.

$Mo_{12}Bi_5Ni_{3.0}Co_{2.0}Fe_{0.4}Na_{0.2}B_{0.2}K_{0.08}Si_{24}$ 500 ml. per reaction tube of an acrolein oxidation catalyst of the composition set forth below was placed in the second-stage reaction vessel similarly as in the first stage, 150 ml. of the catalyst at the inlet part being diluted with 75 ml. of Raschig rings.

$Sb_{100}Ni_{43}Mo_{35}V_7Nb_3Cu_3Si_{80}$ (Oxygen indication omitted)

The first-stage and second-stage reaction vessels were respectively heated to 310° C. and 280° C., and a mixture gas of propylene 10 percent, steam 15 percent, and air 75 percent was preheated to 200° C. beforehand and supplied as a starting gas at a flow rate of 2,240 liter per hour (based on 0° C. and standard atmospheric pressure) to the first-stage reaction vessel. The pressure of the reaction system was maintained at 1.0 kg./cm.² gage. The outlet gas of the second stage was cooled to approximately 40° C. and separated into gas and liquid, and the pressure of the waste gas thus separated was raised by means of a 650 liter/hr. compressor. The waste gas thus pressurized was mixed with 650 liter of air and thus recycled to the nozzle at the first-stage outlet. The stream of the mixture gas with the first-stage formed gases was maintained at approximately 250° C. and supplied to the second-stage reaction vessel.

The results of the reaction were as shown in Table 8. No deterioration whatsoever was observable after the elapse of 60 days. The temperatures at the starting material supplying part and the outlet part of the first stage were stable, and there were no abnormalities.

TABLE 8

| Elapsed time | Propylene conversion (%) | AL conversion (%) | AA yield (%) |
|---|---|---|---|
| 1 day | 98.4 | 99.2 | 83.5 |
| 60 days | 97.9 | 99.0 | 85.5 |

What we claim is:

1. In a process for producing acrylic acid by a two-stage, vapor-phase catalytic oxidation which comprises subjecting a mixture gas of propylene, steam, and air to a first-stage reaction thereby to convert the propylene into, principally, acrolein and subjecting the gaseous product formed in the first-stage reaction to a second-stage reaction thereby to convert the acrolein into, principally, acrylic acid, in the presence of a multicomponent catalyst which comprises molybdenum and/or vanadium capable of providing a conversion of acrolein of 90% or more at a reaction temperature of about 220 to 340 C with a contact time of about 0.5 to 6 seconds, the improvement which comprises carrying out said oxidation under the conditions:

A. that a composite oxide catalyst expressed by the formula

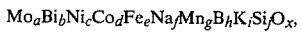

$Mo_aBi_bNi_cCo_dFe_eNa_fMn_gB_hK_iSi_jO_x$, where a through x represent atomic ratios of the respective elements, and, when a is 12, b is 4 through 7, c is 0.05 through 5, d is 0.05 through 5, e is 0.05 through 2, f is 0 through 1, g is 0 through 1, (f+g) is 0.01 through 1, h is 0.02 through 2, i is 0 through 1, j is 6 through 48, and x is a number satisfying the valence of an element other than oxygen, is used in the first-stage reaction;

B. that (1) the composition of said mixture gas supplied to a bed of the catalyst in the first-stage reaction is characterized by an oxygen/propylene mol ratio of (1.1 to 2.0)/1, a propylene concentration of 7 to 13 percent, and a steam concentration of 2 to 30 percent, the temperature of the mixture gas prior to its introduction into the catalyst bed being 260° C. or lower, and (2) the reaction conditions on the first-stage catalyst bed are a reaction temperature of 260° to 370° C. and a contact time of 1 to 8 seconds; and C. that a second mixture gas of the gaseous product formed in the first-stage reaction and a gas resulting from addition of air or oxygen gas to a waste gas separated from gaseous product formed in the second-stage reaction is supplied to a bed of the catalyst in the second-stage reaction, (1) the oxygen content of the second mixture gas being such that the mol ratio X/Y, wherein X is the sum of the quantity of oxygen in the mixture gas subjected to the first-stage reaction and the quantity of oxygen thus added to the waste gas, and Y is the quantity of propylene in the mixture gas subjected to the first-stage reaction, will be (1.6 to 2.8)/1, and (2) the temperature of the second mixture gas prior to its introduction into the second-stage catalyst bed being 280° C. or lower, said waste gas being a portion of a waste gas which results from cooling of the gaseous product formed in the second-stage reaction and removal therefrom of a greater part of the acrylic acid therein by condensation.

2. The process as claimed in claim 1 in which the composition of said mixture gas supplied to a bed of the catalyst in the first stage reaction is characterized by an oxygen/propylene mol ratio of 1.2 to 1.8)/1, a propylene concentration of 8 to 12 percent and a steam concentration of 5 to 25% and the temperature of the mixture gas prior to its introduction into the first stage catalyst bed is about 130° to 250° C.

3. The process as claimed in claim 1, in which on the first stage catalyst bed, the reaction temperature is about 270° to 350° C. and the contact time is about 2 to 6 seconds.

4. The process as claimed in claim 1 in which the oxygen content of the second mixture gas is such that the mol ratio X/Y is (1.7 to 2.6)/1, X and Y being as defined in claim 1.

5. The process as claimed in claim 1 in which the temperature of the second mixture gas prior to its introduction into the second-stage catalyst bed is about 200° to 270° C.

6. The process as claimed in claim 1 in which the second stage reaction is conducted on the presence of a composite oxide catalyst consisting essentially of molybdenum, vanadium, antimony, nickel, niobium and copper at a temperature of about 220° C. to 340° C. for a contact time of about 0.5 to 6 seconds.

7. The process as claimed in claim 6 in which
the composition of said mixture gas supplied to a bed of the catalyst in the first stage reaction is characterized by an oxygen/propylene mol ratio of (1.2 to 1.8)/1, a propylene concentration of 8 to 12 percent and a steam concentration of 5 to 25% and the temperature of the mixture gas prior to its introduction into the first stage catalyst bed is about 130° to 250° C.,
in the first stage catalyst bed, the reaction temperature is about 270° to 350° C. and the contact time is about 2 to 6 seconds,
the oxygen content of the second mixture gas is such that the mol ratio X/Y is (1.7 to 2.6)/1 and
the temperature of the second mixture gas prior to its introduction into the second-stage catalyst bed is about 200° to 270° C.

* * * * *